(12) United States Patent
Solderman et al.

(10) Patent No.: US 9,987,628 B2
(45) Date of Patent: Jun. 5, 2018

(54) CIRCULAR EXTRACTOR

(71) Applicant: GE Healthcare Bio-Sciences AB, Uppsala (SE)

(72) Inventors: Tobias Ingemar Solderman, Uppsala (SE); Nils Norrman, Uppsala (SE); Henrik Ostlin, Uppsala (SE); Susanna Lindman, Uppsala (SE); David Carl Martin Bergman, Uppsala (SE); Peter Mats Oliviusson, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 87 days.

(21) Appl. No.: 15/101,337

(22) PCT Filed: Nov. 26, 2014

(86) PCT No.: PCT/EP2014/075697
§ 371 (c)(1),
(2) Date: Jun. 2, 2016

(87) PCT Pub. No.: WO2015/086324
PCT Pub. Date: Jun. 18, 2015

(65) Prior Publication Data
US 2016/0303559 A1    Oct. 20, 2016

(30) Foreign Application Priority Data
Dec. 13, 2013    (GB) .................................. 1322081.9

(51) Int. Cl.
B01L 3/00 (2006.01)
G01N 35/00 (2006.01)
(Continued)

(52) U.S. Cl.
CPC .............. B01L 3/5025 (2013.01); B01L 3/502 (2013.01); B01L 3/5085 (2013.01);
(Continued)

(58) Field of Classification Search
CPC ....... B01L 2200/028; B01L 2200/0621; B01L 2300/0803; B01L 2300/0858;
(Continued)

(56) References Cited

U.S. PATENT DOCUMENTS

| | | |
|---|---|---|
| 3,547,547 A | 12/1970 | Anderson |
| 3,771,878 A | 11/1973 | Molloy et al. |

(Continued)

FOREIGN PATENT DOCUMENTS

| | | |
|---|---|---|
| CH | 693689 A5 | 12/2003 |
| WO | 2005/093053 A1 | 10/2005 |

OTHER PUBLICATIONS

International Search Report and Written Opinion regarding International Application No. PCT/EP2014/075697, dated Feb. 13, 2015, 9 pages.

(Continued)

*Primary Examiner* — Jennifer Wecker
(74) *Attorney, Agent, or Firm* — Eversheds Sutherland (US) LLP

(57) ABSTRACT

The present invention provides methods and systems for eluting and an analyte from a solid phase. The invention further provides methods and systems for transferring liquid analyte reagent mixtures from a solid phase to a second vessel, such as a microtiter plate well. The invention is useful in the manipulation of biological molecules such as nucleic acids, carbohydrates, proteins and peptides. In particular, the invention has utility for manipulating proteins and peptides in isoelectric focusing gels.

23 Claims, 8 Drawing Sheets

(51) Int. Cl.
  *G01N 21/07* (2006.01)
  *B04B 5/04* (2006.01)
  *G01N 35/10* (2006.01)
  *G01N 27/447* (2006.01)
  *G01N 35/04* (2006.01)

(52) U.S. Cl.
  CPC .......... *B01L 3/50855* (2013.01); *G01N 21/07* (2013.01); *G01N 35/00* (2013.01); *B01L 2200/028* (2013.01); *B01L 2200/0621* (2013.01); *B01L 2200/0631* (2013.01); *B01L 2300/0803* (2013.01); *B01L 2300/087* (2013.01); *B01L 2300/0858* (2013.01); *B01L 2300/0864* (2013.01); *B01L 2300/0887* (2013.01); *B01L 2400/0406* (2013.01); *B01L 2400/0478* (2013.01); *G01N 27/44739* (2013.01); *G01N 35/1065* (2013.01); *G01N 2035/00108* (2013.01); *G01N 2035/0439* (2013.01)

(58) Field of Classification Search
  CPC ....... B01L 2300/087; B01L 2300/0887; B01L 2400/0478; B01L 3/502; B01L 3/5025; B01L 3/5085; B01L 3/50855; B01L 2300/0864; B01L 2400/0406; B01L 2200/0631; G01N 2035/00108; G01N 2035/0439; G01N 21/07; G01N 27/44739; G01N 35/00; G01N 35/1065
  See application file for complete search history.

(56) References Cited

U.S. PATENT DOCUMENTS

| | | | |
|---|---|---|---|
| 4,234,799 A * | 11/1980 | Okumura | B04B 5/04 250/576 |
| 2003/0223912 A1* | 12/2003 | Knecht | B01L 3/50255 422/400 |
| 2005/0048597 A1 | 3/2005 | Smith et al. | |

OTHER PUBLICATIONS

GB Search Report regarding GB Application 1322081.9, dated Sep. 1, 2014, 3 pages.

\* cited by examiner

CIRCULAR EXTRACTOR

CROSS-REFERENCE TO RELATED APPLICATIONS

This application is a filing under 35 U.S.C. 371 of international application number PCT/EP2014/075697, filed Nov. 26, 2014, which claims priority to GB application number 1322081.9, filed Dec. 13, 2013, the entire disclosures of each of which are hereby incorporated by reference.

TECHNICAL FIELD OF THE INVENTION

The present invention relates to the field of biomolecule processing and in particular to methods and systems for the elution and transfer of biomolecules separated on a solid phase. The invention provides methods and systems for transferring eluted liquid analyte reagent mixtures comprising biomolecule fragments from a solid phase to a vessel, such as a microtitre plate well.

DESCRIPTION OF RELATED ART

To allow determination of the identity and composition of a biological molecule such as a protein, peptide or nucleic acid, the biological molecule is first cut up into fragments by either enzymatic or chemical means. Taking proteins as an example, a common approach is to use enzymes which cut the protein at specific amino acid residues, a typical example being trypsin which hydrolyses the protein after lysine or arginine residues. When tryptic digestion is carried out on a sample containing a very limited number of proteins, it is possible to determine the identity of the protein present from the masses of the peptides resulting from the digestion, e.g. using mass spectrometry (MS). A sample applied to a matrix-assisted laser desorption/ionization (MALDI) MS target is only allowed to contain a limited number of peptides and similarly electrospray ionization (ESI) MS can only accept a limited number of peptides per time unit. The sample is normally a very complex mixture containing many thousands of proteins which after digestion could easily correspond to one hundred thousand to 10 more than one million peptides. Rigorous separation of the peptides is therefore required prior to characterisation and quantification.

The separation of biological molecules, prior to or in parallel with their identification and quantification, can be achieved by a variety of techniques including electrophoretic and chromatographic methods. Electrophoresis is a technique which is commonly used to separate biological molecules on the basis of their size and/or their charge. Electrophoretic techniques like iso-electric focusing (IEF) and polyacrylamide gel electrophoresis (PAGE) generally give much better resolution and yields than chromatographic alternatives. High Resolution IEF (HiRIEF) separates peptides based on their isoelectric point (pI) using immobilised pH gradient (IPG) strips. The first step separates peptides in an IEF instrument and in a second step the IPG strip is moved to an extractor that dissolves the peptides in liquid and moves the liquid to a standard microplate format supported by most liquid chromatography (LC) and MS instruments. 2-D electrophoresis based on the combination of IEF and PAGE is also a commonly used approach when separation of very complex samples is conducted.

The disadvantages with electrophoretic techniques are however that they are labour intensive, often demand craftsmanship and that they are hard to automate.

One solution that has been put forward that aims to address the disadvantages associated with electrophoretic techniques is the peptide extractor instrument described in WO 2006/1136296 and WO 2006/1136297. A straight wellformer is mounted on each IPG strip and transfers peptides from the well-former to the microplate. With this technique, however, several operations are still required. In addition, the established way of transferring with a needle robot depends on a series of time consuming transfers from gel strip with mounted well-former to the microplate. Extraction and transfer of peptides from an IPG strip to a microplate using known methods involves use of a manual pipette or a needle robot. There are normally 2-8 IPG strips with 72 fractions each that should be made solvable by adding a liquid. Adding and extracting the liquid should be done several times to optimize transfer of sample. The samples need to diffuse for some time after adding the liquid and before extracting the sample in the liquid.

There is therefore a need for less labour-intensive and less time-consuming methods for the extraction and transfer of biological molecules from a solid phase on which they have been separated.

SUMMARY OF THE INVENTION

This invention describes systems and methods useful in the extraction and transfer of biomolecule samples in a solid phase to a container such as a microplate for further analysis such as using liquid chromatography (LC) and MS instrumentation. In particular the present invention provides an apparatus for eluting an analyte from a solid phase where samples can be processed in parallel thereby providing a less labour intensive and time consuming method compared with known methods.

In one aspect the present invention provides a wellformer (1) for use with an apparatus (100) for eluting an analyte from a solid phase (8) wherein said wellformer (1) comprises a cylindrical body (2) having a top surface (3), a bottom surface (4), a circumferential surface (5) and a plurality of chambers (6) wherein each of said plurality of chambers (6) defines an opening on each of said top surface (3), said bottom surface (4) and said circumferential surface (5), thereby defining a plurality of openings on each of said top surface (23), said bottom surface (24) and said circumferential surface (25).

In one embodiment of said wellformer (1) said plurality of openings on said top surface (23) are located the same distance from the circumferential surface (5) of the cylindrical body (2) as each other.

In one embodiment of said wellformer (1) said plurality of openings on said bottom surface (24) are located the same distance from the circumferential surface (5) of the cylindrical body (2) as each other.

In one embodiment of said wellformer (1) each of said plurality of openings on said top surface (23) is in direct overlying registry with the corresponding of said plurality of openings on said bottom surface (24).

In one embodiment of said wellformer (1) said plurality of openings on said circumferential surface (25) are located the same distance from the top surface (3) of the cylindrical body (2) as each other.

In one embodiment of said wellformer (1) each of said plurality of chambers (6) defines a T-shape extending between said top surface (3), said bottom surface (4) and said circumferential surface (5).

In one embodiment said wellformer (1) further comprises a compression ring (7) positioned in overlying registry with said plurality of openings on said circumferential surface (5).

In one embodiment said wellformer (1) further comprises said solid phase (8) sandwiched between said compression ring (7) and said circumferential surface (5) and positioned in overlying registry with said plurality of openings on said circumferential surface (5).

In one embodiment of said wellformer (1) said solid phase (8) is an electrophoresis gel or blotting membrane.

In one embodiment of said wellformer (1) said solid phase (8) is a strip.

In one embodiment of said wellformer (1) said strip is an immobilized pH gradient (IPG) strip.

In one embodiment of said wellformer (1) said cylindrical body comprises a central opening (9) extending from said top surface (3) to said bottom surface (4).

In another aspect the present invention provides an apparatus (100) for eluting an analyte from a solid phase (108) wherein the analyte has been separated along a separation direction on said solid phase (108) wherein said apparatus (100) comprises a wellformer (101) as defined hereinabove and a plurality of liquid distribution channels (110) in fluid communication with a plurality of chambers (106) in said wellformer (101) wherein each of said plurality of liquid distribution channels (110) defines an inlet (111) proximal to one of said plurality of chambers (106) and an outlet (112) fluidly connected to said inlet (111) by a passageway (113) extending therebetween.

In one embodiment of said apparatus (100) each of said plurality of liquid distribution channels (110) extends outwards from each of said plurality of chambers (106) of said wellformer (101).

In one embodiment of said apparatus (100) each of said plurality of liquid distribution channels (110) extends in a straight line and is the same length as each other of said plurality of liquid distribution channels (110).

In one embodiment of said apparatus (100) said plurality of liquid distribution channels (110) are defined by a stack of laminated foils (114).

In one embodiment of said apparatus (100) said stack of laminated foils (114) is supported by a base (115).

In one embodiment of said apparatus (100) said outlet (112) of each of said plurality of liquid distribution channels (110) is fluidly connected to a collection chamber (116).

In one embodiment of said apparatus (100) said collection chamber (116) is a microtitre plate well.

In one embodiment of said apparatus (100) said microtire plate well is provided as part of a bendable row of microtitre plate wells (117).

In one embodiment said apparatus (100) further comprises a rod head (118) positioned in overlying registry with said top surface (103) of said cylindrical body (102) of said wellformer (101) wherein said rod head (118) comprises a plurality of rods (119) each of which fits into one of said plurality of chambers (106) of said wellformer (101) via one of said plurality of openings on said top surface (123) of said wellformer (101) and exerts pressure into said plurality of chambers (106) to facilitate elution of said analyte.

In relation to any corresponding features, further embodiments of the apparatus of the invention are as defined hereinabove in relation to the wellformer of the invention.

In a further aspect the present invention provides a method for eluting an analyte from a solid phase (8) wherein said analyte has been separated along a separation direction in said solid phase (8), wherein said method comprises:

(i) providing a wellformer (1) as defined herein above;
(ii) positioning said solid phase (8) comprising said separated analyte in overlying registry with said plurality of openings on said circumferential surface (5) of said cylindrical body (2) of said wellformer (1);
(iii) positioning a compression ring (7) in overlying registry with said said solid phase (8) in order that said solid phase (8) is sandwiched between said circumferential surface (5) of said cylindrical body (2) of said wellformer (1) and said compression ring (7)
(iv) eluting said analyte from said solid phase (8).

In one embodiment the method of the invention further comprises the exertion of pressure into said plurality of chambers (6) by means of positioning a rod head (118) into the said plurality of openings on said top surface (23) of said cylindrical body (2) of said wellformer (1) to facilitate elution of said analyte.

In one embodiment of the method of the invention said eluting step is followed by a further step (iv) of transferring said eluted analyte along a plurality of liquid distribution channels (110).

In one embodiment of the method of the invention each of said plurality of liquid distribution channels (110) is fluidly connected to a collection chamber (116) as defined hereinabove and wherein said method further comprises transfer of said eluted analyte from said plurality of chambers via said plurality of liquid distribution channels (110) into said collection chambers (116).

In relation to any corresponding features, further embodiments of the method of the invention are as defined hereinabove in relation to either the wellformer or the apparatus of the invention.

DETAILED DESCRIPTION OF THE PREFERRED EMBODIMENTS

Figure 1:
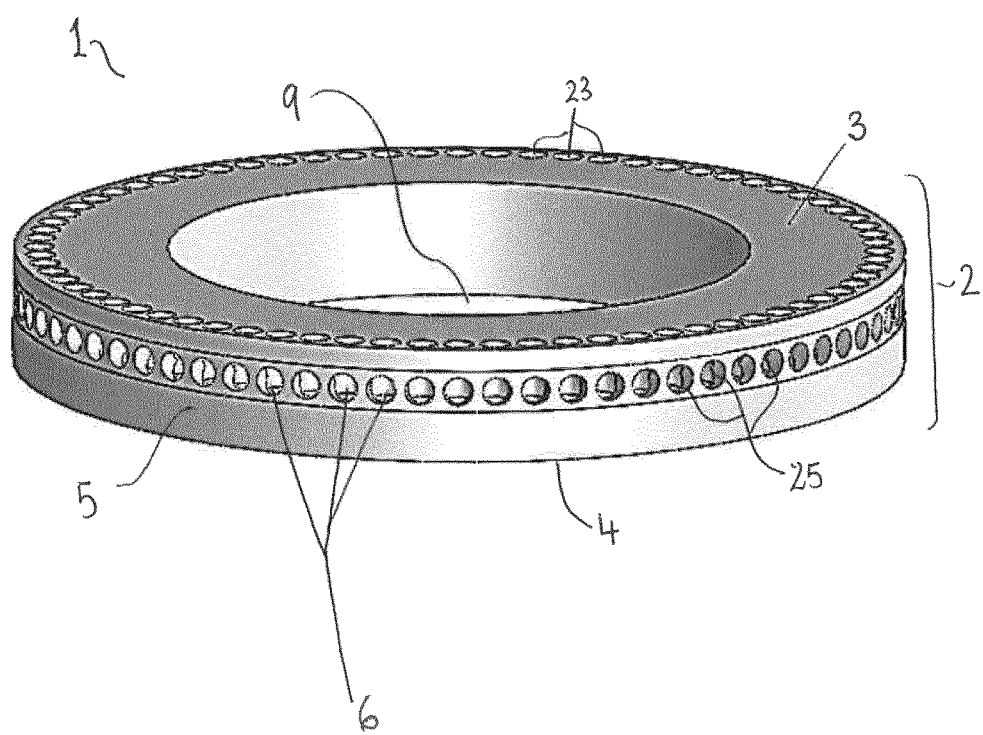
FIG. 1 illustrates a wellformer of the invention showing details of the cylindrical body.

FIG. 1 illustrates an exemplary wellformer (1) of the invention, showing the cylindrical body (2) with its top (3), bottom (4) and circumferential (5) surfaces, and central opening (9). The plurality of chambers (6) cannot be seen in their entirety but are indicated as being within the openings on the circumferential surface (25). The openings on each of the surfaces are present at regular intervals all the way around the cylindrical body (2). In the diagram three of the openings on the top surface (23) and on the circumferential surface (25) are indicated. The openings on the bottom surface (4) are not visible in this diagram but would be positioned in direct underlying registry with said openings on said top surface (23), thereby defining in each case an open-ended cylindrical passageway from the top (3) surface to the bottom surface (4), which in addition includes another passageway to the circumferential surface (5) so that the chamber (6) is substantially T-shaped.

Figure 2:
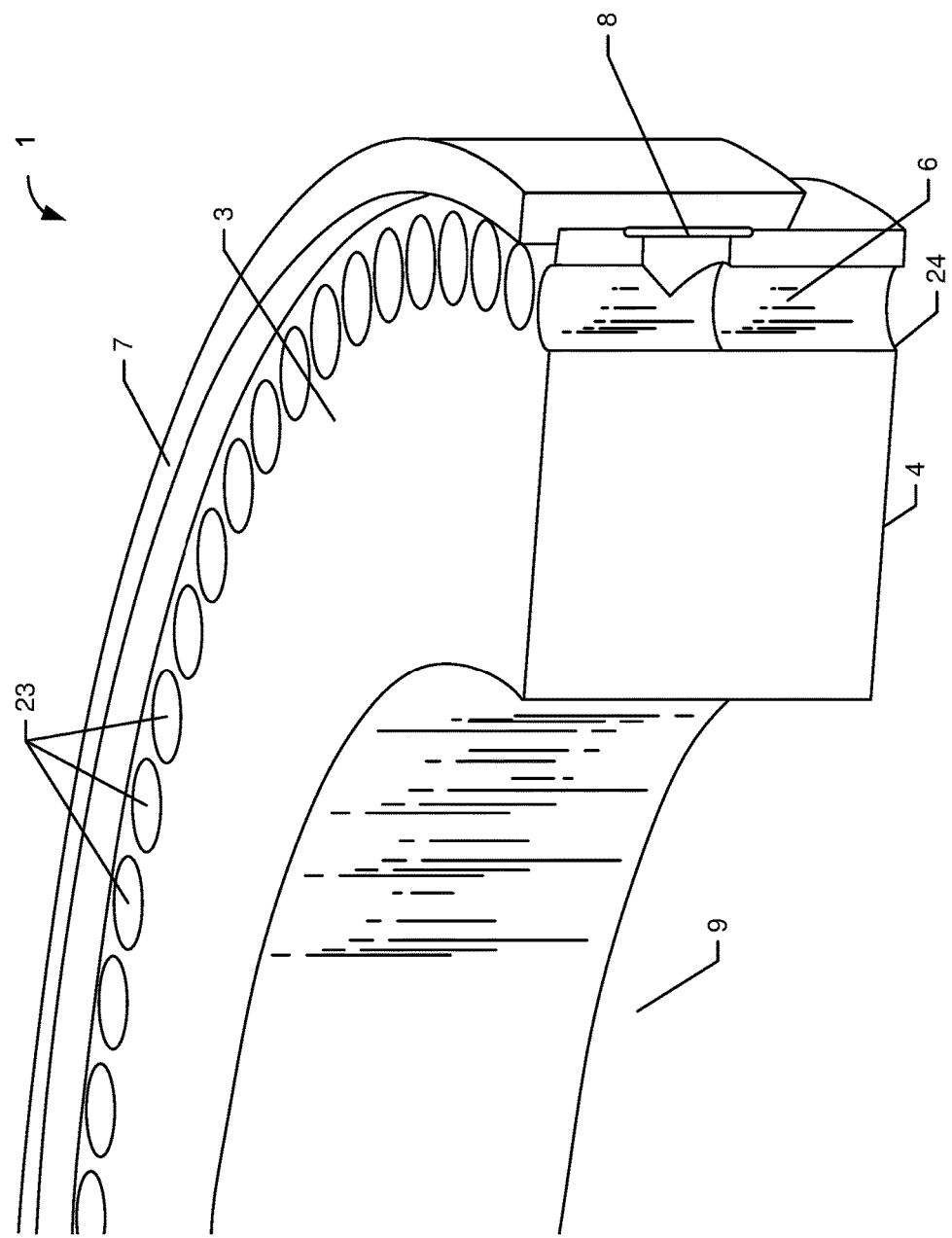
FIG. 2 illustrates a sectional view of a wellformer of the invention showing certain features of the cylindrical body in more detail and also including the solid phase and compression ring.

FIG. 2 shows a close-up section of the wellformer (1) of the invention where one of the T-shaped chambers (6) is illustrated in cross-section. Additionally included in FIG. 2 is the solid phase (8) in the form of a strip sandwiched between the cylindrical body (2) of the wellformer (1) and the compression ring (7). In this arrangement it can be appreciated that the compression ring (7) acts to hold the solid phase (8) in place to facilitate elution of analyte.

The "analyte" present in the solid phase is a biomolecule such as a protein, peptide or nucleic acid. Before processing on the wellformer, the analyte has been separated along a separation direction on said solid phase (8). Typically, the analyte is cleaved into fragments before being applied to the solid phase for separation. Cleavage can be carried out by any number of well-known methods, e.g. for DNA molecules, the DNA can be cut into smaller fragments using a DNA restriction endonuclease (or restriction enzyme), for proteins an enzyme which cuts the protein at specific amino acid residues can be used, a typical example being trypsin. Separation on the solid phase may be carried out wherein the solid phase is an electrophoresis gel or blotting membrane. In one embodiment said solid phase comprising said separated analyte is in the form of a strip when positioned on the wellformer (1) of the present invention. It is envisaged that either the solid phase is in strip form when the separation is carried out, e.g. where the strip is an immobilized pH gradient (IPG) strip, or the solid phase is converted into strip form following separation, i.e. where the solid phase is in a planar or slab form that is subsequently cut into strips. In the case where a slab is cut into strips care needs to be taken to ensure the solid phase is not contaminated with other biomolecules during processing, e.g. from the operator, from instruments used or from the environment. Methods to avoid contamination are well known to those of skill in the art such as set out in the WHO "Handbook: good laboratory practice (GLP): quality practices for regulated non-clinical research and development" (2nd ed. 2009) which can be found at this link: http://www.who.int/tdr/publications/documents/glp-handbook.pdf.

Figure 3:
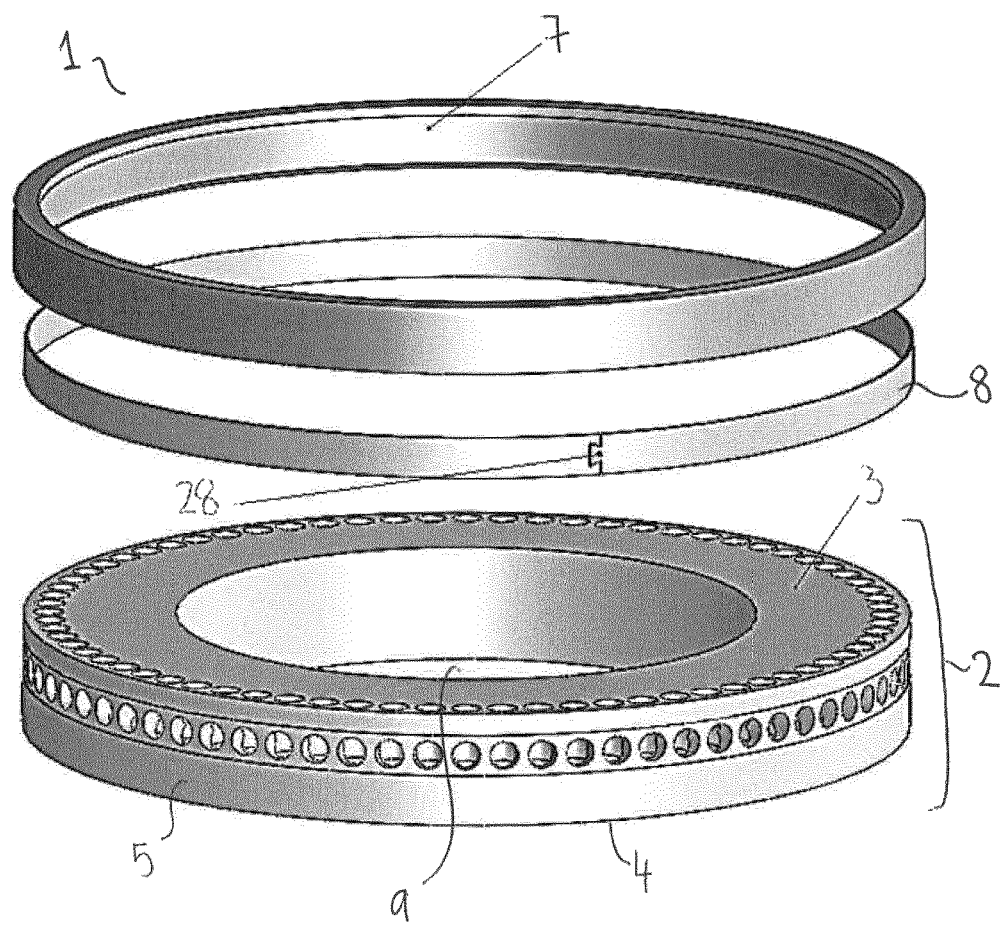
FIG. 3 shows a deconstructed view of the wellformer that is shown in cross section in FIG. 2.
Figure 4:
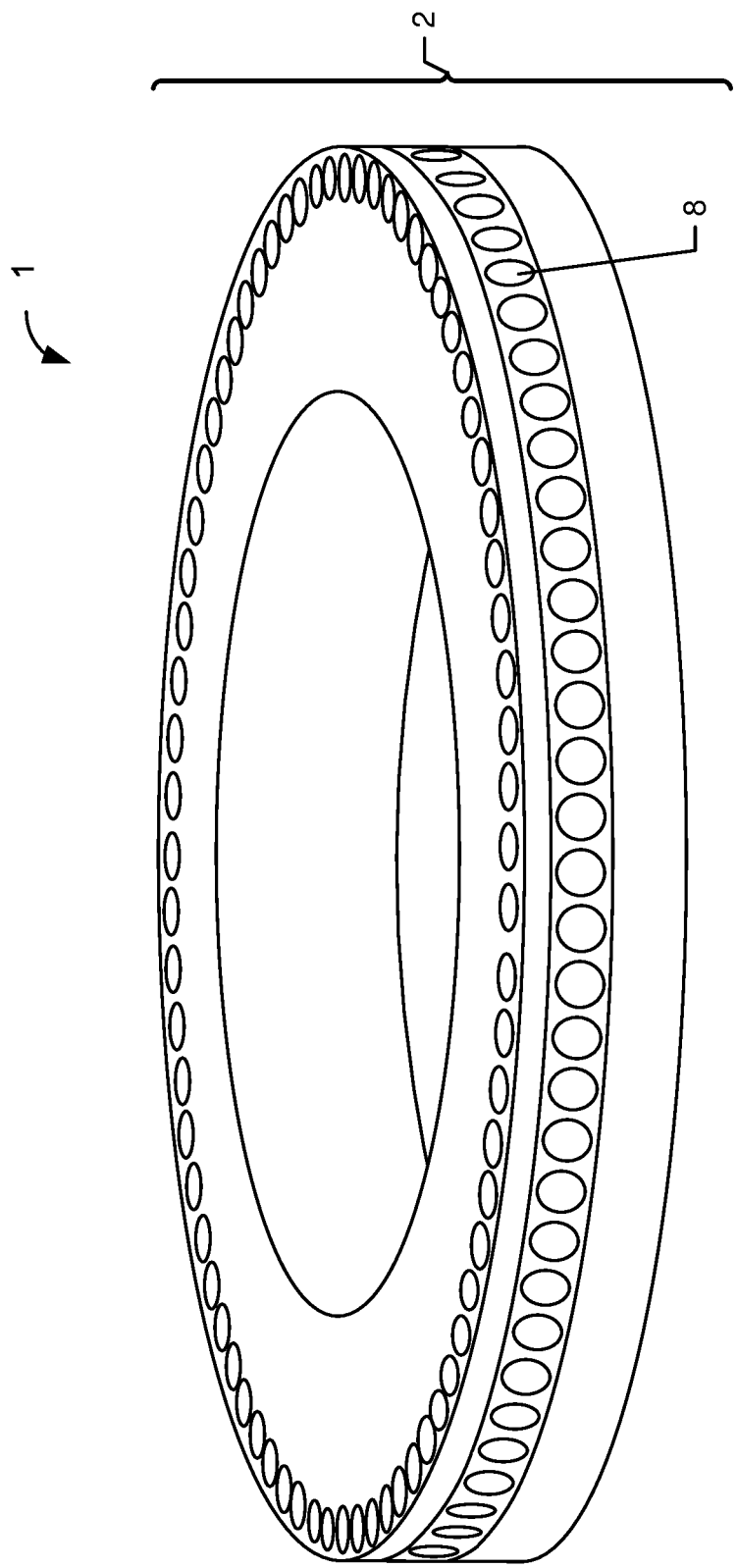
FIG. 4 shows a wellformer of the invention when the solid phase has been put in place.
Figure 5:
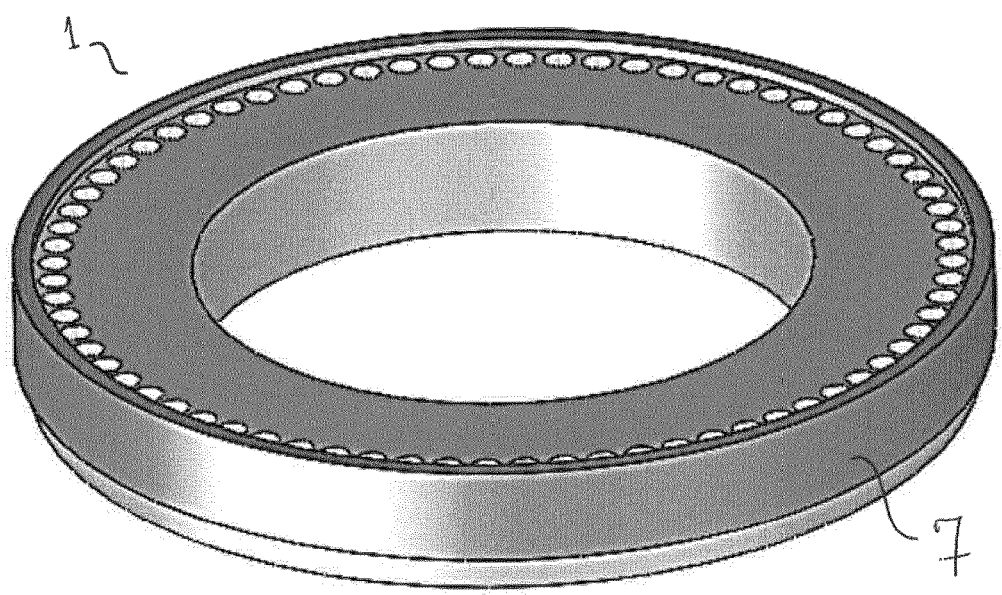
FIG. 5 shows a wellformer of the invention where both the solid phase and the compression ring have been put in place.

FIG. 3 illustrates the same elements as shown in FIG. 2 prior to placement of the solid phase (8) and compression ring (7) onto the cylindrical body (2). The strip connection (28) is visible, which converts the strip to a ring that can be easily placed on the cylindrical body (2). In operation, the strip (8) is put in place prior to the compression ring (7) in order to arrive at the arrangement of FIG. 2. FIG. 4 shows the cylindrical body with just the solid phase (8) in place. FIG. 5 illustrates how the wellformer of FIG. 2 would look in its entirety.

Figure 6:
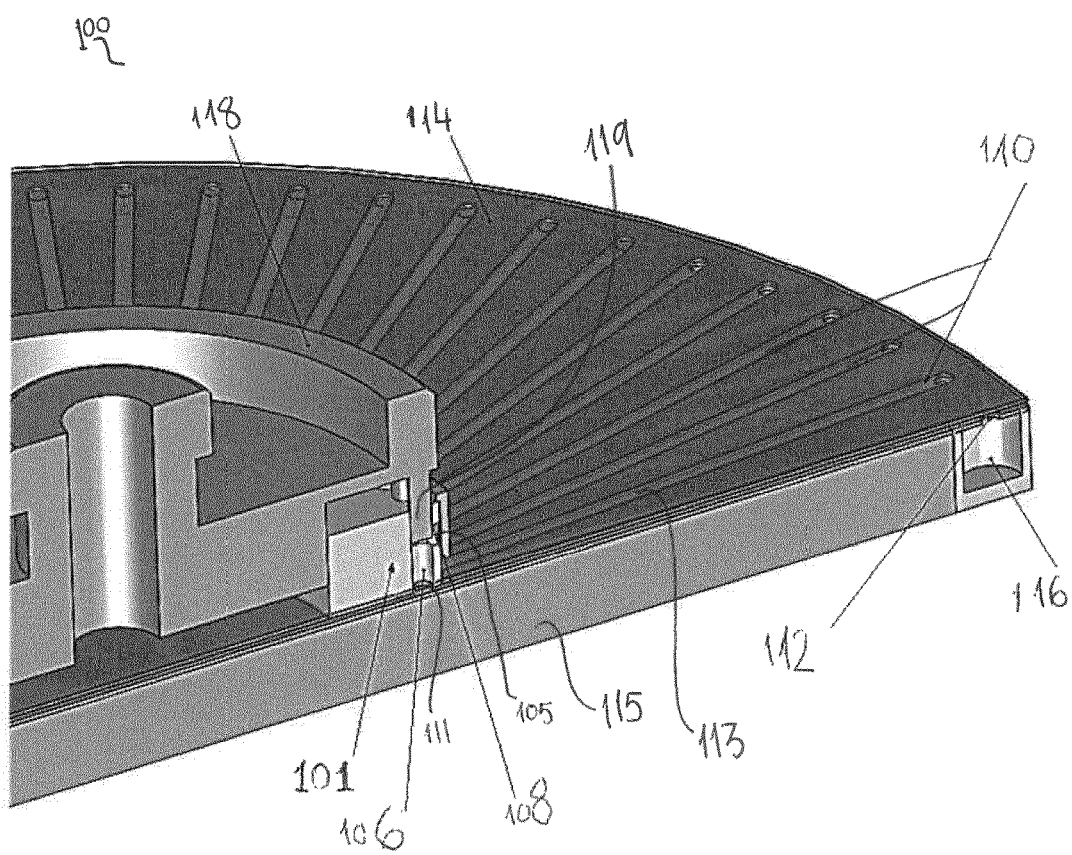
FIG. 6 illustrates an apparatus of the invention including the rod head for exerting pressure on the chamber in which the analyte is eluted from the solid phase as well as liquid distribution channels for transferring the eluted analyte from the chamber to a collection chamber which is a microplate well.

FIG. 6 shows an exemplary apparatus (100) of the invention. An exemplary wellformer (101) of the invention is in place at a central location of the apparatus (100) and sitting on top of a stack of laminated foils (114) which themselves are supported by a base (115). The laminated foils (114) define a series of liquid distribution channels (110), three of which are indicated in FIG. 6. These liquid distribution channels (110) are arranged at regular intervals and radiating out from the wellformer (101). Each liquid distribution channel (110) includes an inlet (111) proximal to one of said plurality of chambers (106) of said wellformer (101), and an outlet (112) distal to said wellformer (101) wherein said inlet (111) and outlet (112) are fluidly connected by a passageway (113) extending therebetween. With this arrangement the analyte eluted from the solid phase (8) can pass from a chamber (106) and into a liquid distribution channel (110) via one of the inlets (111) and thereby along a passageway (113) to arrive at an outlet (112) where the eluted analyte can be collected in a suitable collection chamber (116). In FIG. 6 the collection chamber (116) is a microtitre plate well. Elution of the analyte from the solid phase is facilitated by exerting pressure into each chamber (106) by means of a rod head (118), which is illustrated in position in the apparatus (100) of FIG. 6. The rod head (118) includes a plurality of rods (119) extending down into said plurality of chambers (106) of said wellformer (101). In FIG. 6 the rods (119) are of a cylindrical shape that matches the shape of the chambers (106) so that the rods (119) fit compatibly therein.

Figure 7:
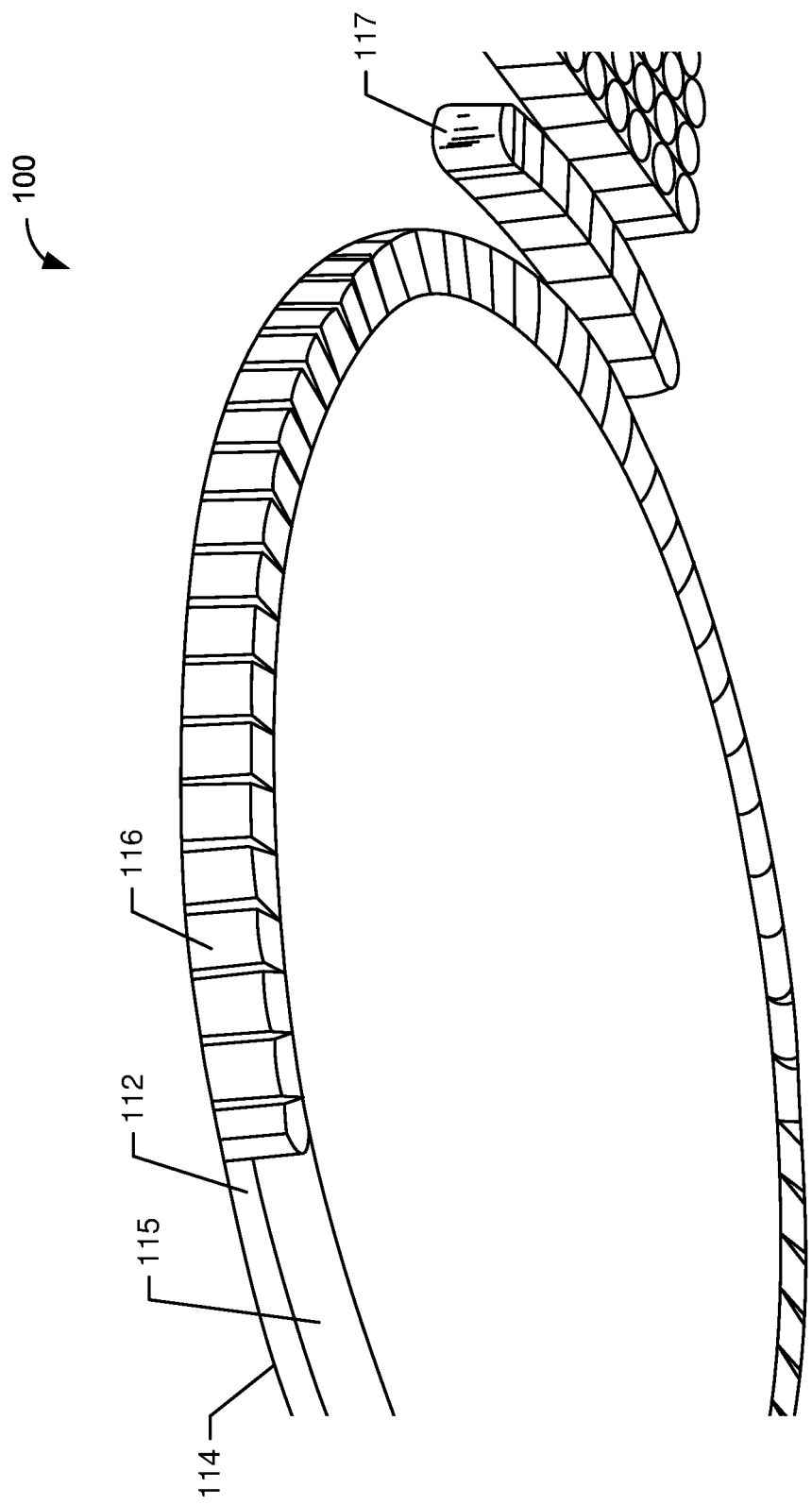
FIG. 7 shows how bendable strips of microplate wells can be arranged in an apparatus of the invention.

FIG. 7 provides an underside view of the apparatus (100) of the invention showing the stack of laminate foils (114) sitting on top of base (115) and showing several of the plurality of outlets (112) of the liquid distribution channels. FIG. 7 provides an illustration of how microtitre plate wells (116) can be used in the form of bendable rows (117) to attach to the edge of the apparatus (100). Conveniently, these bendable rows (117) of microtire plate wells are easily detached from the apparatus (100) to form a group of microtitre plate wells that can be organised into the form of a standard microtitre plate by placing them into a suitable frame. In this way the eluted analyte can be readily analysed by a variety of well-known means adapted to receive a microtitre plate.

Figure 8:
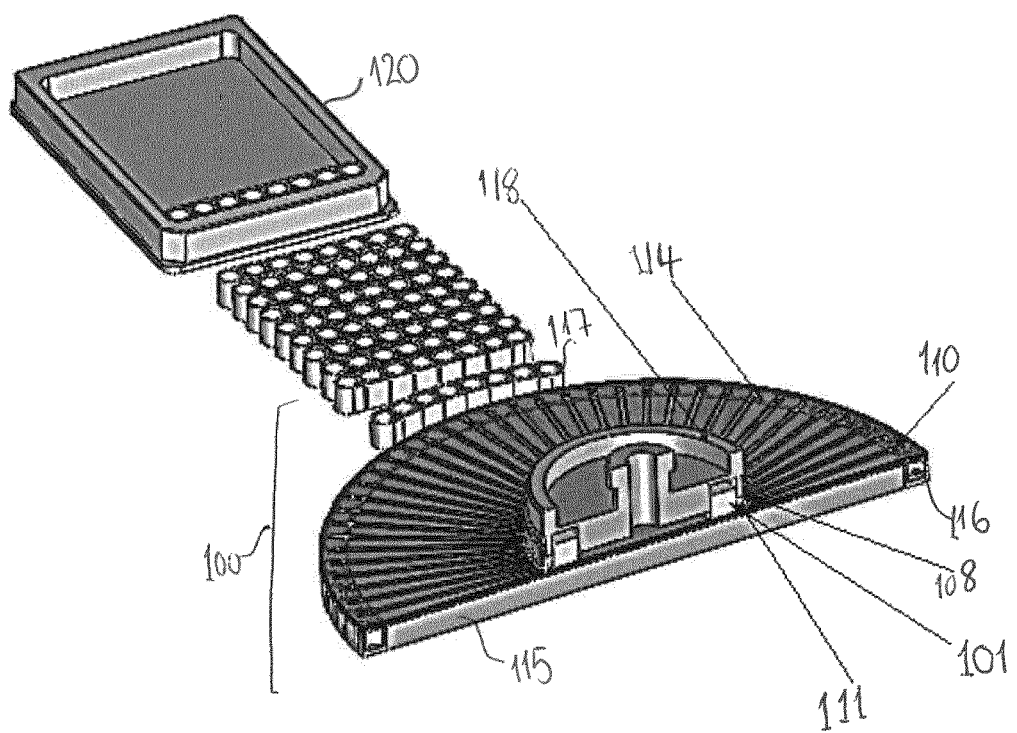
FIG. 8 shows how the bendable strips of microplate wells can be easily assembled into microplate form permitting direct transfer to the next stage of processing.

FIG. 8 provides a more detailed illustration of how the bendable rows (117) of microtitre plate wells detach and are subsequently arranged in a frame (120) to form a microtitre plate. In FIG. 8 one half of the apparatus (100) of the invention is shown in cross-section showing the relative placement of the various features.

In one embodiment the apparatus (100) of the invention is in a circular format for receipt of an IPG strip containing separated peptides onto the wellformer. When the peptides have dissolved using a suitable eluent, pressure is used to push the dissolved peptides through a circular transfer plate into microtitre plate wells on the edge of the apparatus, i.e. the disk fringe. These microtitre plate wells are connected through a hinge and attached to a transfer plate. After complete transfer, the microtitre plate wells can be detached and put into a microtitre plate frame giving the same microtitre plate format as standard microtitre plate enabling further processing in LC-MS/MS instrumentation. The advantage is simultaneous extraction of peptides into a standard microtitre plate format decreasing transfer time compared to the known needle system. The transfer plate and foldable microtitre plate can be made disposable which also minimizes washing time.

The eluting step of the method of the invention is carried out by means of a suitable buffer. Suitable elution buffers could be 0-xx % of an organic/inorganic acid in water or 0-xx % of an organic solvent in water. Non-limiting examples of acid include formic acid, acetic acid, phosphoric acid and the like; the skilled person will be aware of others that are suitable. Non-limiting examples of organic solvent include acetonitrile, methanol, ethanol and the like; the skilled person will be aware of others that are suitable. For the % acid a typical but non-limiting concentration would be up to 0.1%. For the organic solvent a typical but non-limiting concentration would be up to 5.0%.

And for organic solvent up to 5% but not the exact limit Elution buffer is added to each chamber in the wellformer one or more times so that the analyte elutes from the solid phase and into the elution buffer.

In the evaluation of a particular biomolecule only a subset thereof is generally of interest to take through to evaluation using e.g. LC-MS/MS applications. So for example to select and transfer peptides located in a subset of fractions in the wellformer it is important to know the peptide isoelectric point (pI) range for each fraction. The pI for the peptide of interest can be determined by using predicting algorithms or prior experimental database lookup. An IPG strip has a unique pI gradient due to manufacturing, to determine each fraction range an internal standard fluorescent marker can be used. The present invention may thus include a detector custom made for automatic detection of a fluorescent marker in the wellformer. The goal is to detect in which fractions markers with known pI are located. Quantification of the markers is of no interest. The detection principle is almost identical to a fluorescent microscope.

The detector can use a standard laser to excite a fluorescent marker present on the biomolecule (e.g. a Cy5 marked peptide). A laser fluorescent clean up filter is necessary to prevent laser from disturbing in the fluorescent emission spectra where detection will take place. In the optical path of the detector, an emission filter blocks laser spectra and lets through the fluorescent marker emission spectra. The detector (which can be a photo-diode, PMT etc) measures the emitted light.

There are three methods of transporting light to/from sample, 1: laser-fibre-sample-fibre-detector, 2: laser-fibre-sample-lenses-detector, 3: laser-sample-lenses-detector.

For method 1 the detector package is moved to the fraction position on the wellformer. The laser light can be transported to wellformer fraction through an optical fibre, the sample is excited and emits light which is collected by an optical fibre transporting light to a emission filter and then to focusing lens and then to the detector. One drawback is the high angle of incidence to the emission filter with decreased filter performance as a result. A light collection lens before the collecting optical fibre can be necessary.

For method 2 laser light is transported to the sample as in method 1. The emitted fluorophore light needs to be collected using a lens at a focus distance from the sample. Light is transported with parallel rays through an emission filter and finally through a lens focusing light on the detector. The emitted light angle is limited by the wellformer so it is important when collecting light without the optical fibre to be positioned straight above sample.

For method 3 laser at a specific angle is used to bounce the light on the wellformer walls to the sample in the wellformer fraction. Light is detected as in method 2. A beamsplitter reflecting laser light to sample at the same optical path as emitted light can also be used (identical to a fluorescent microscope principle).

The invention claimed is:

1. An extractor for use with an apparatus for eluting an analyte from a solid phase wherein said extractor comprises a cylindrical body having a top surface, a bottom surface, a circumferential surface and a plurality of chambers wherein each of said plurality of chambers defines an opening on each of said top surface, said bottom surface and said circumferential surface, thereby defining a plurality of openings on each of said top surface, said bottom surface and said circumferential surface;

wherein the extractor further comprises a compression ring; and wherein during use said solid phase being sandwiched between said compression ring and said circumferential surface, such that said compression ring is positioned in overlying registry with said plurality of openings of said circumferential surface.

2. The extractor as defined in claim 1 wherein said plurality of openings on said top surface are located the same distance from the circumferential surface of the cylindrical body as each other.

3. The extractor as defined in claim 1 wherein said plurality of openings on said bottom surface are located the same distance from the circumferential surface of the cylindrical body as each other.

4. The extractor as defined in claim 1 wherein each of said plurality of openings on said top surface is in direct overlying registry with the corresponding of said plurality of openings on said bottom surface.

5. The extractor as defined in claim 1 wherein said plurality of openings on said circumferential surface are located the same distance from the top surface of the cylindrical body as each other.

6. The extractor as defined in claim 1 wherein each of said plurality of chambers defines a T-shape extending between said top surface, said bottom surface and said circumferential surface.

7. The extractor as defined in claim 1 wherein said solid phase is an electrophoresis gel or blotting membrane.

8. The extractor as defined in claim 1 wherein said solid phase is a strip.

9. The extractor as defined in claim 8 wherein said strip is an immobilized pH gradient (IPG) strip.

10. The extractor as defined in claim 1 wherein said cylindrical body comprises a central opening extending from said top surface to said bottom surface.

11. An apparatus for eluting an analyte from a solid phase wherein the analyte has been separated along a separation direction on said solid phase wherein said apparatus comprises an extractor as defined in claim 1 and a plurality of liquid distribution channels in fluid communication with a plurality of chambers in said extractor wherein each of said plurality of liquid distribution channels defines an inlet proximal to one of said plurality of chambers and an outlet fluidly connected to said inlet by a passageway extending therebetween.

12. The apparatus as defined in claim 11 wherein each of said plurality of liquid distribution channels extends outwards from each of said plurality of chambers of said extractor.

13. The apparatus as defined in claim 12 wherein each of said plurality of liquid distribution channels extends in a straight line and is the same length as each other of said plurality of liquid distribution channels.

14. The apparatus as defined in claim 13 wherein said plurality of liquid distribution channels are defined by a stack of laminated foils.

15. The apparatus as defined in claim 14 wherein said stack of laminated foils is supported by a base.

16. The apparatus as defined in claim 15 wherein said outlet of each of said plurality of liquid distribution channels is fluidly connected to a collection chamber.

17. The apparatus as defined in claim 16 wherein said collection chamber is a microtitre plate well.

18. The apparatus as defined in claim 17 wherein said microtire plate well is provided as part of a bendable row of microtitre plate wells.

19. The apparatus as defined in claim 18 further comprising a rod head positioned in overlying registry with said top surface of said cylindrical body of said extractor wherein said rod head comprises a plurality of rods each of which fits into one of said plurality of chambers of said extractor via one of said plurality of openings on said top surface of said extractor and exerts pressure into said plurality of chambers to facilitate elution of said analyte.

20. A method for eluting an analyte from a solid phase wherein said analyte has been separated along a separation direction in said solid phase, wherein said method comprises:
   (i) providing an extractor as defined in claim 1;
   (ii) positioning said solid phase in overlying registry with said plurality of openings on said circumferential surface of said cylindrical body of said extractor;
   (iii) positioning the compression ring in overlying registry with said solid phase in order that said solid phase is sandwiched between said circumferential surface of said cylindrical body of said extractor and said compression ring; and
   (iv) eluting said analyte from said solid phase.

21. The method as defined in claim 20 which further comprises the exertion of pressure into said plurality of chambers by means of positioning a rod head into the said plurality of openings on said top surface of said cylindrical body of said extractor to facilitate elution of said analyte.

22. The method as defined in claim 21 wherein said eluting step of said method is followed by a further step (iv) of transferring said eluted analyte along a plurality of liquid distribution channels.

23. The method as defined in claim 22 wherein each of said plurality of liquid distribution channels is fluidly connected to a collection chamber and wherein said method further comprises transfer of said eluted analyte from said plurality of chambers via said plurality of liquid distribution channels into said collection chambers.

\* \* \* \* \*